(12) United States Patent
Link et al.

(10) Patent No.: US 11,266,450 B2
(45) Date of Patent: Mar. 8, 2022

(54) ARTHRODESIS PLATE

(71) Applicant: Waldemar Link GmbH & Co. KG, Hamburg (DE)

(72) Inventors: Helmut D. Link, Hamburg (DE); Jan Teuber, Norderstedt (DE)

(73) Assignee: WALDEMAR LINK GmbH & Co. KG, Hamburg (DE)

( * ) Notice: Subject to any disclaimer, the term of this patent is extended or adjusted under 35 U.S.C. 154(b) by 95 days.

(21) Appl. No.: 16/349,566

(22) PCT Filed: Mar. 9, 2018

(86) PCT No.: PCT/EP2018/055899
§ 371 (c)(1),
(2) Date: May 13, 2019

(87) PCT Pub. No.: WO2018/188861
PCT Pub. Date: Oct. 18, 2018

(65) Prior Publication Data
US 2020/0179019 A1 Jun. 11, 2020

(30) Foreign Application Priority Data
Apr. 11, 2017 (EP) .................................... 17165943

(51) Int. Cl.
*A61B 17/80* (2006.01)
*A61F 2/42* (2006.01)
*A61F 2/30* (2006.01)

(52) U.S. Cl.
CPC ........ *A61B 17/8061* (2013.01); *A61F 2/4241* (2013.01); *A61F 2002/3093* (2013.01);
(Continued)

(58) Field of Classification Search
CPC ........ A61F 2/42; A61F 2/4225; A61F 2/4241; A61F 2/4606; A61F 2002/30136;
(Continued)

(56) References Cited

U.S. PATENT DOCUMENTS 9,474,561 B2 * 10/2016 Shemwell .......... A61B 17/8605
9,622,783 B2 *  4/2017 Reiley ................ A61F 2/30771
(Continued)

FOREIGN PATENT DOCUMENTS

CN      101325927 A    12/2008
CN      204562343 U     8/2015
(Continued)

OTHER PUBLICATIONS

International Search Report and Written Opinion dated Jun. 12, 2018 in corresponding International Application No. PCT/EP2018/055899.
(Continued)

*Primary Examiner* — Eric S Gibson
(74) *Attorney, Agent, or Firm* — Joseph V. Saphia; Haug Partners LLP

(57) ABSTRACT

The invention relates to an arthrodesis plate for the stiffening of joints, in particular finger joints, comprising a proximal and distal anchoring region which are connected to one another in a mechanically rigid manner, characterised in that at least one outer contour of one of the two anchoring regions has a cross-section which is undulating, for example roof-shaped, or is provided with alternating crests and troughs by means of coating, and/or has a transversal-sagittal cross-section.

11 Claims, 2 Drawing Sheets

(52) U.S. Cl.
CPC ............... *A61F 2002/30136* (2013.01); *A61F 2002/30265* (2013.01); *A61F 2002/30622* (2013.01); *A61F 2002/30904* (2013.01); *A61F 2002/4243* (2013.01); *A61F 2310/00023* (2013.01)

(58) Field of Classification Search
CPC .... A61F 2002/30265; A61F 2002/4228; A61F 2002/4233; A61F 2002/4238; A61F 2002/4243; A61F 2002/4251; A61F 2002/4253; A61F 2002/4256; A61F 2002/4258
See application file for complete search history.

(56) References Cited

U.S. PATENT DOCUMENTS

| | | | | |
|---|---|---|---|---|
| 9,675,392 B2* | 6/2017 | Shemwell | ........... | A61B 17/8605 |
| 2004/0167625 A1* | 8/2004 | Beyar | ................. | A61B 17/7266 |
| | | | | 623/11.11 |
| 2007/0156241 A1* | 7/2007 | Reiley | ................. | A61B 17/1615 |
| | | | | 623/17.11 |
| 2007/0282443 A1* | 12/2007 | Globerman | ........ | A61B 17/1671 |
| | | | | 623/17.11 |
| 2010/0125301 A1* | 5/2010 | Kinmon | ............. | A61B 17/1757 |
| | | | | 606/300 |
| 2011/0118796 A1* | 5/2011 | Reiley | ................. | A61B 17/1682 |
| | | | | 606/86 R |
| 2013/0066435 A1 | 3/2013 | Averous et al. | | |
| 2015/0073413 A1* | 3/2015 | Palmer | ............... | A61B 17/7291 |
| | | | | 606/63 |
| 2016/0367300 A1* | 12/2016 | Caldarella | ............ | A61B 17/808 |
| 2017/0007416 A1* | 1/2017 | Sander | ................... | A61F 2/4225 |
| 2017/0181770 A1* | 6/2017 | Reiley | ................. | A61B 17/1682 |
| 2020/0179019 A1* | 6/2020 | Link | .................. | A61B 17/8061 |

FOREIGN PATENT DOCUMENTS

| | | |
|---|---|---|
| CN | 205339255 U | 6/2016 |
| CN | 106344218 A | 1/2017 |
| DE | 20 2009 008872 U1 | 9/2000 |
| EP | 2 158 864 A2 | 3/2010 |
| WO | WO-2015147846 A1 * | 1/2015 |

OTHER PUBLICATIONS

Office Action issued in the corresponding Chinese Patent Application No. 201880023361.4 dated Mar. 3, 2021.

* cited by examiner

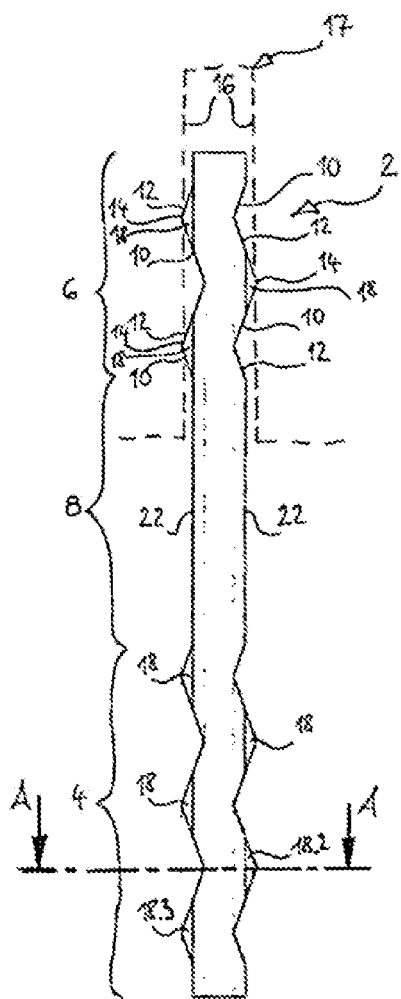
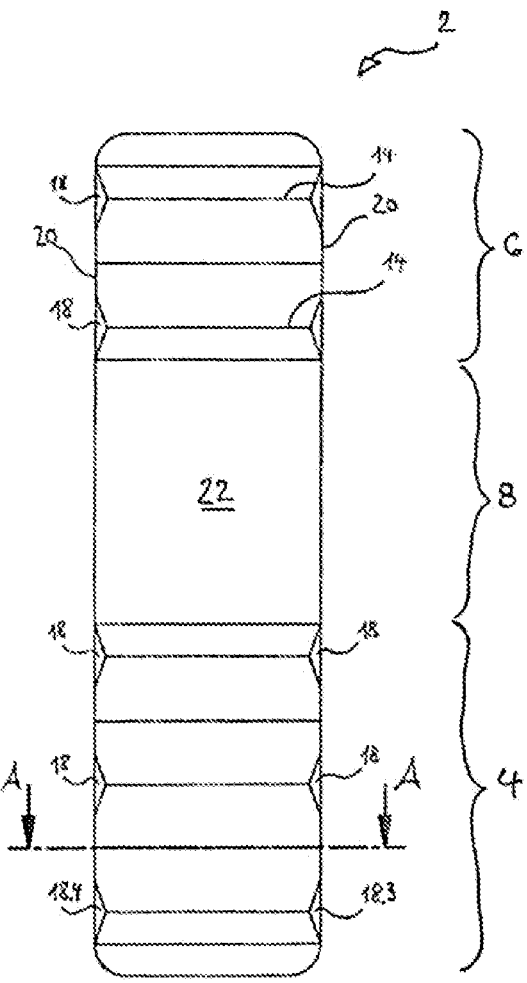
Fig. 1a    Fig. 1b
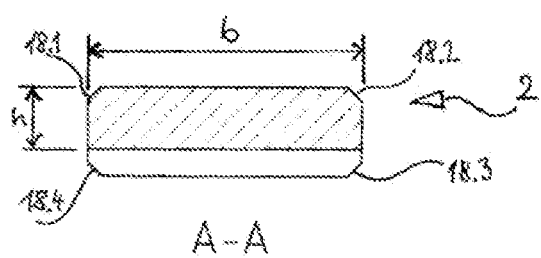
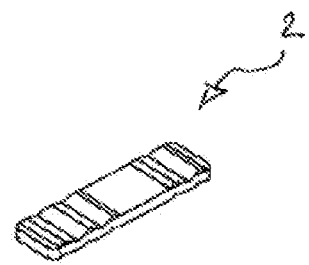
Fig. 1c    Fig. 2

ARTHRODESIS PLATE

This application is the National Stage entry under 35 U.S.C. § 371 of International Application No. PCT/EP2018/055899 filed on Mar. 9, 2018, published on Oct. 18, 2018 under Publication Number WO 2018/188861, which claims the benefit of priority under 35 U.S.C. § 119 of European Patent Application Number 17165943.6 filed Apr. 11, 2017, the entireties of which are herein incorporated by reference.

The invention relates to an arthrodesis plate for the stiffening of joints, in particular finger joints, comprising a proximal and distal anchoring region which are connected to one another in a mechanically rigid manner.

Joint prostheses as well as osteosynthesis plates are used in orthopaedic and trauma surgery. The latter are also used in a special application for the planned stiffening (arthrodesis) of damaged joints. The attachment of such implants by the surgeon should be as quick, simple and minimally invasive as possible, with arthrodesis plates also having to be anchored to the affected bone in such a manner that forces between the bone and implant are reliably and long-lastingly transferred.

As is well known, prostheses also for finger joints are anchored, for instance, in the medullary cavity without screws. Arthrodesis implants are normally screwed to the bone from the outside. The palmar or dorsal access normally required for the cited anchoring methods furthermore carries the risk of injuring the flexor and/or extensor tendons.

The object forming the basis for the present invention is to provide an arthrodesis plate, in particular for finger joints, which is improved in terms of its handling during surgical attachment and in terms of its anchoring.

This object is solved according to the invention by means of an arthrodesis plate having the features of claim 1. Advantageous embodiments are specified in the sub-claims.

The arthrodesis plate according to the invention is used to stiffen joints, in particular finger joints, but also other joints that predominantly have a hinge joint function. It comprises a proximal and distal anchoring region which are connected to one another in a mechanically rigid manner. According to the invention, the arthrodesis plate is characterised in that at least one outer contour of one of the two anchoring regions has an undulating sagittal cross-section (i.e. an undulating cross-section in a plane lying parallel to the sagittal plane).

In addition to continuous (for example sinusoidal) wave crests and troughs, the term "undulating", in the context of the present invention, also includes other notch-shaped contours, for example roof-shaped or sawtooth-shaped contours. This means that the outer contour of the anchoring region does not necessarily have to extend in round, continuous wave crests and troughs. Instead, the rising and falling sides of the undulating outer contour can also be configured so as to be linear, linear in parts, even undulating and/or discontinuous in any manner. In other words, the outer contour of the anchoring region does not have to be continuously curved in the geometric sense in the region of its crests and troughs, but can also be configured in a discontinuous manner. The crests and troughs of the outer contour can thus also have the shape of an edge such that the undulating cross-section takes the form of a corner or point and constitutes a point-like or sharp-edged change in direction. The undulating outer contour according to the invention can thus be technically generated, for example, by applying a coating to an initially flat outer contour, for example using a plasma spray process. If the plasma spray process is controlled in such a manner that different coating thicknesses are achieved at different points of the anchoring region, an undulating contour can be produced. In this case as well, the shape of a wave crest (i.e. of a locally highest area of the outer contour) can be configured, depending on the shape of the applied particles, to be rounded in any manner, but can also be configured to be, for example, angular or with an otherwise discontinuously curved surface. The same applies to the wave troughs (i.e. the locally deepest areas of the outer contour).

The arthrodesis plate according to the invention, when designed in this manner, is configured for the following and thus enables in the following manner the anchoring of an implant according to the invention (in particular also for the arthrodesis of a distal interphalangeal joint or a proximal interphalangeal joint) in the bone ends that are to be mechanically connected with one another (rigidly for arthrodesis) by means of the arthrodesis plate according to the invention: the surgeon can produce from the medial or lateral (for example by means of a milling tool or an oscillating saw) a level slot (that preferably lies in the frontal plane of the finger bone and extends approximately through the central axis thereof) in both the proximal as well as the distal bone end (of the bones to be rigidly connected with one another by means of the implant) that is facing the joint defect—which slot particularly preferably does not pass entirely through the bone in the other direction (lateral or medial). The surgeon can now insert into this cut from the same side (medial or lateral) one of the two anchoring regions (preferably having a transversal cross-section that is broader (in the mediolateral direction) than it is high (in the palmar-dorsal direction), in particular a flat, rectangular transversal cross-section). When doing so, he only has to take into consideration less relevant structures medially or laterally on the finger. There is thus no danger, as was the case with conventional implants, of traumatising the palmar or dorsal structures. When inserting the anchoring region into the flat slot from the medial or lateral, an angle-stable connection (in particular in the sagittal plane) is created between the implant and the end of the bone—and surprisingly even a connection that is secure against extraction forces—namely due to a "press fit" (or, in technical engineering terms, due to interference fit): for this purpose, the width (height) of the flat slot is to be configured by the surgeon so as to be (slightly) smaller than the height preferably of a plurality of the cross-sections of the anchoring region (configured according to the invention to be transversally preferably less high than wide). This procedure as described so far (creation of a flat slot in the end of the bone; insertion of the anchoring region into the flat slot from the medial or lateral) is repeated at the other end of the bone for the other anchoring region of the implant—to attach the implant for arthrodesis. The two anchoring regions that are in this way connected in an angle-stable and non-extractable manner to the two bone ends are, according to the invention, connected to one another in a mechanically rigid manner, namely at 180° to one another (i.e. in a straight line) or alternatively at an arbitrary angle (in particular 30°). Mounted in this manner, the implant according to the invention rigidly bridges the two ends of the bone for arthrodesis.

Thus, the two anchoring regions of the arthrodesis plate according to the invention are in particular configured to each be anchored in a flat slot (which is to be produced in the bone to be treated by a surgeon), namely by means of a press fit (friction fit or interference fit), with the height of (preferably a plurality of) cross-sections of the respective anchoring region being greater than the height (width) of the respective slot.

The arthrodesis plate according to the invention is thus in particular configured to be anchored by means of a press fit in a flat slot in each of the two bone ends in the frontal plane of the finger bone and approximately through the central axis thereof. According to the invention, this anchoring is further facilitated by the fact that at least one outer contour of one of the two anchoring regions has an undulating sagittal cross-section within the meaning of the present invention. This cross-section may, for example, also be zigzag-shaped with straight rising sides and straight falling sides. This undulating cross-section is in particular configured to press via its wave crests into the cutting surfaces or boundary surfaces of the flat slot. This can strengthen the press fit locally, i.e. at the wave crests—and can also ensure a form fit by pressing the wave crests into the cutting surfaces.

What is preferred according to the invention to facilitate the press fit anchoring is an arthrodesis plate in which both the top side and the bottom side of the anchoring regions overall have an undulating sagittal cross-section—and can thus press over the entire surface (that is to say preferably over the entire length in the longitudinal direction of the implant, i.e. usually in the proximal-distal direction, and/or over the entire width of the implant, i.e. usually in the lateral direction) into the upper and lower cutting surface of the flat slot.

It is then particularly preferred that the undulating sagittal cross-section of the top side and the bottom side extend parallel to one another at least in sections, preferably overall. The result is thus not only an undulating sagittal cross-section of an anchoring region outer contour, but of the anchoring region as a whole.

These and other features of the invention are described in the following with reference to the enclosed drawings of embodiment examples of the invention. In these drawings FIG. 1a shows a representation of an arthrodesis plate according to the invention in a side view from the lateral of a sagittal plane, FIG. 1b shows a representation of the arthrodesis plate according to the invention in a top view of a frontal plane from the front, FIG. 1c shows a sectional representation of the arthrodesis plate according to the invention as a section in a transversal plane in a view from the distal, and FIG. 2 shows a three-dimensional view of the arthrodesis plate according to the invention as shown in FIG. 1.

Figure 3:
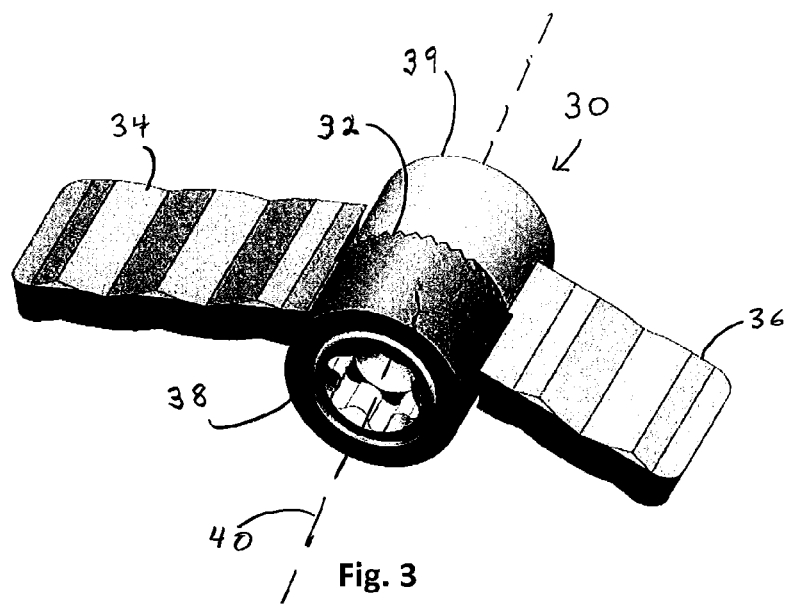
FIG. 3 shows an alternative embodiment of an arthrodesis plate.

Shown in FIGS. 1 and 2 is an arthrodesis plate 2. The arthrodesis plate 2 is used to stiffen joints, in particular finger joints (not shown). It comprises a proximal anchoring region 4 and a distal anchoring region 6 as well as a shaft region 8 that connects the two anchoring regions with one another in a mechanically rigid manner. The two anchoring regions 4, 6 have transversal cross-sections (one is shown in FIG. 1c) which are wider (b, in the lateral direction) than they are high (h, in the palmar-dorsal direction).

The outer contours 10, 12 of the two anchoring regions 4, 6 overall have an undulating cross-section (FIG. 1a) in planes parallel to the sagittal plane. The cross-section is zigzag-shaped with straight rising sides 10 and straight falling sides 12. This undulating cross-section is in particular also configured to press via its "wave crests" 14 into the flat cutting surfaces 16 of a flat slot (17; only shown schematically with dashed lines). This can facilitate a local press fit, i.e. at the wave crests 14, and also ensure a form fit with the slot 17 by pressing the wave crests 14 into the cutting surfaces 16. Both the top side and bottom side of the anchoring regions 4, 6 overall have the undulating sagittal cross-section 10, 12: The top side and bottom side overall extend almost entirely parallel to one another.

Each transversal cross-section (one is shown in FIG. 1c) of the two anchoring regions 4, 6 is rectangular, with corners of some of the rectangular transversal cross-sections having chamfers 18 (rounded edges (not shown) are also alternatives according to the invention), namely in the region of all of the wave crests 14.

The volume of the two anchoring regions 4, 6 extends linearly in the proximal-distal direction with straight side edges 20 (FIG. 1b). The volume of the shaft region also extends linearly in the proximal-distal direction with straight side edges 20 in one direction and also in alignment with the extension direction of the volume of the two anchoring regions, namely with common straight side edges 20. Alternatively (not shown), the shaft region may have a kink in its extension in the proximal-distal direction, which orients the two anchoring regions at an angle to one another in the sagittal plane (FIG. 1a) (which angle can preferably be 1° to 40° or 5° to 35° or 30° in particular for arthrodesis at the proximal interphalangeal joint—or 1° to 50° or 5° to 45° or 30° for arthrodesis at the distal interphalangeal joint). Such a configuration results in an implant that is particularly suitable for the arthrodesis of the interphalangeal joints since in this area, arthrodeses of finger joints are usually performed in a flexion position having such dimensions.

The shown implant 2 is intended as a permanent implant and for this purpose is made of a titanium alloy. The surfaces are rough ($R_a$>4) in order to promote the accumulation and growth of bone. The surfaces are coated with a growth-promoting coating (not shown; for example calcium phosphate).

The shown implant 2 has the following dimensions, which have proven to be effective for use as an arthrodesis plate at the DIP joint. The thickness h of the overall flat rectangular cross-section (FIG. 1c) of implant 2 is 1.6 mm (preferably between 1.4 and 1.8 mm), the width b is 7 mm (preferably between 6 and 8 mm). The total length of implant 2 is 26 mm (preferably between 20 and 30 mm). The teeth or wave crests project 0.5 mm beyond the planes of the top sides 22 (preferably between 0.2 and 1.0 mm), the wave troughs are 0.5 mm deep (preferably between 0.1 and 1.0 mm). The sides 10, 12 have an inclination angle of 30° (preferably between 20° and 40°) to the planes of the top sides 22 (frontal planes).

Figure 4:
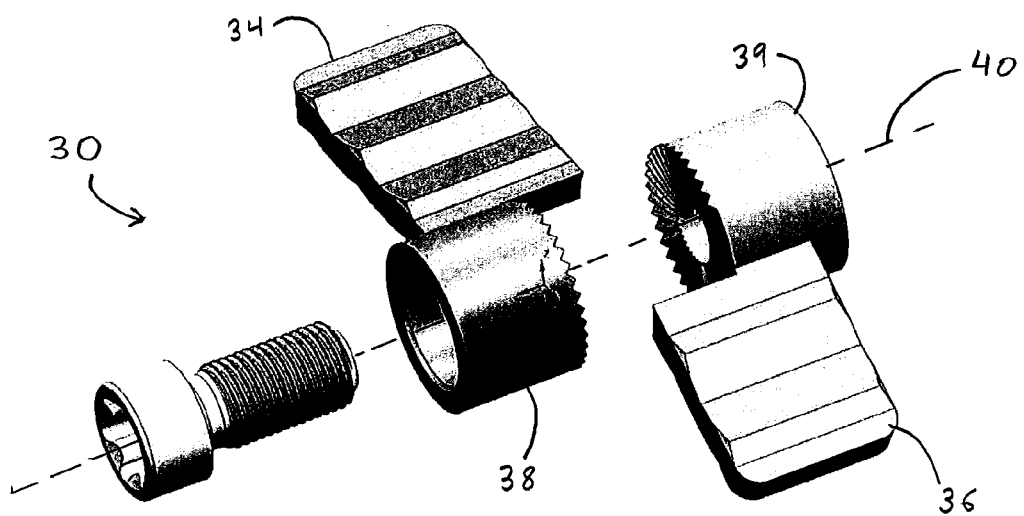
FIG. 4 shows the arthrodesis plate of FIG. 3 in an exploded view.

Shown in FIGS. 3 and 4 is an alternative embodiment of an arthrodesis plate 30, wherein a pivotable and lockable connection 32 is formed between the two anchoring regions 34, 36, which makes the angle adjustable. In an exemplary embodiment, the lockable connection 32 may comprise complementary contact surfaces 38, 39 lying one on top of the other with star-shaped textures about a pivot axis 40, and/or the contact surfaces 38, 39 can be locked together in a form-fit and/or friction-fit manner. As FIGS. 3 and 4 depict, the anchoring regions 34, 36 are oriented at an angle to each other.

The invention claimed is:

1. An arthrodesis plate for stiffening of finger joints, the arthrodesis plate comprising:
   a longitudinal direction in a proximal-distal direction, a width direction in a mediolateral direction, and a height direction in a palmar-dorsal direction, wherein a length of the arthrodesis plate in a longitudinal direction is larger than a width of the arthrodesis plate in the width direction and wherein the width is larger than a height of the arthrodesis plate in the height direction, a proximal anchoring region and a distal anchoring region which are connected to one another in a mechanically rigid manner, wherein a width of a transversal cross-section of the anchoring regions, the transversal cross-section being defined by the width and height directions, is greater than a height of the transversal cross-section, wherein the proximal and distal anchoring regions have at least one of a sagittal cross-section, the sagittal cross-section being defined by the longitudinal and height directions, and the transversal cross-section an undulating outer contour, and wherein the anchoring regions of the arthrodesis plate are insertable into a flat slot in the mediolateral direction, wherein the undulating outer contour is configured to press via its wave crests into boundary surfaces of the flat slot in the palmar-dorsal direction so that the anchoring regions are secured by a friction fit.

2. The arthrodesis plate according to claim 1, wherein the anchoring regions are adapted to be anchored by way of a press fit in a flat slot in each of the two bone ends of a joint defect intended for arthrodesis by means of the arthrodesis plate.

3. The arthrodesis plate according to claim 1, wherein a top side and bottom side of the anchoring regions have an undulating sagittal and/or transversal cross-section.

4. The arthrodesis plate according to claim 3, wherein the undulating sagittal and/or transversal cross-section of the top side and bottom side extend parallel to one another at least in sections.

5. The arthrodesis plate according to claim 3, wherein the undulating sagittal and/or transversal cross-section is zig-zag-shaped with straight rising sides and straight falling sides.

6. The arthrodesis plate according to claim 1, wherein the transversal cross-section which is rectangular.

7. The arthrodesis plate according to claim 6, wherein corners of the rectangular transversal cross-section and/or edges of the arthrodesis plate have chamfers and/or are rounded.

8. The arthrodesis plate according to one of the claim 1, wherein a volume of the two anchoring regions extends substantially linearly in the proximal-distal direction or that the two anchoring regions are oriented at an angle to one another.

9. The arthrodesis plate according to claim 8, wherein the angle is 1° to 50°, or 5° to 45°, or 30°.

10. The arthrodesis plate according to claim 9, wherein a pivotable and lockable connection is formed between the two anchoring regions, which makes the angle adjustable.

11. The arthrodesis plate according to claim 10, characterised in that the lockable connection comprises complementary contact surfaces lying one on top of the other with star-shaped textures about a pivot axis, and/or can be locked in a form-fit and/or friction-fit manner.

* * * * *